(12) United States Patent
Perozziello

(10) Patent No.: US 10,646,282 B2
(45) Date of Patent: May 12, 2020

(54) OXYGEN PERMEABLE CONTACT LENS STRUCTURES FOR THICK PAYLOADS

(71) Applicant: Spy Eye, LLC, Los Gatos, CA (US)

(72) Inventor: Eric Anthony Perozziello, Discovery Bay, CA (US)

(73) Assignee: Tectus Corporation, Saratoga, CA (US)

(*) Notice: Subject to any disclaimer, the term of this patent is extended or adjusted under 35 U.S.C. 154(b) by 284 days.

(21) Appl. No.: 15/872,809

(22) Filed: Jan. 16, 2018

(65) Prior Publication Data

US 2018/0203252 A1     Jul. 19, 2018

Related U.S. Application Data

(60) Provisional application No. 62/447,844, filed on Jan. 18, 2017.

(51) Int. Cl.
| | |
|---|---|
| *A61B 34/20* | (2016.01) |
| *A61B 34/30* | (2016.01) |
| *A61B 90/00* | (2016.01) |
| *G02C 7/04* | (2006.01) |

(Continued)

(52) U.S. Cl.
CPC .............. *A61B 34/20* (2016.02); *A61B 34/30* (2016.02); *A61B 34/76* (2016.02); *A61B 90/37* (2016.02); *G02C 7/049* (2013.01); *A61B 2034/2065* (2016.02); *A61B 2090/3983* (2016.02); *G02B 1/043* (2013.01); *G02C 2202/16* (2013.01); *G06T 2207/10016* (2013.01)

(58) Field of Classification Search
CPC ...... G02B 5/18; G02B 5/1809; G02B 5/1828; G02B 5/1842; G02B 5/1847; G02B 5/188; G02B 2005/1804; G02C 7/04

USPC .................................................. 351/159.02
See application file for complete search history.

(56) References Cited

U.S. PATENT DOCUMENTS

| | | |
|---|---|---|
| 4,486,577 A | 12/1984 | Mueller et al. |
| 4,594,401 A | 6/1986 | Takahashi et al. |
| 4,954,587 A | 9/1990 | Mueller |

(Continued)

OTHER PUBLICATIONS

Harvitt, D.M. et al., "Re-Evaluation of the Oxygen Diffusion Model for Predicting Minimum Contact Lens Dk/t Values Needed to Avoid Corneal Anoxia," Optometry and Vision Science, 1999, pp. 712-719, vol. 76, No. 10.

(Continued)

*Primary Examiner* — William R Alexander
*Assistant Examiner* — Henry A Duong
(74) *Attorney, Agent, or Firm* — Fenwick & West LLP

(57) ABSTRACT

A variable geometry contact lens structure having a thickness t sufficient to carry an active payload is constructed using layers of materials with high oxygen transmissibility and low oxygen transmissibility. The low transmissibility layer provide mechanical support for the active payload, and the high transmissibility layers provide adequate oxygen transmission to the cornea of the user's eye. The ratio of the thicknesses of the two layers changes abruptly at the boundaries between the payload and non-payload regions of the structure. For example, at a boundary of the payload region, a ratio of thicknesses of the high transmissibility layer t1 to thickness of the low transmissibility layer t2, R=t1/t2, changes by at least 2:1 over a lateral distance of not more than t.

20 Claims, 8 Drawing Sheets

(51) Int. Cl.
*A61B 34/00* (2016.01)
*G02B 1/04* (2006.01)

(56) References Cited

U.S. PATENT DOCUMENTS

| | | |
|---|---|---|
| 5,548,352 A | 8/1996 | Dewey |
| 8,153,726 B2 | 4/2012 | Hoffman |
| 8,786,675 B2 | 7/2014 | Deering |
| 8,911,078 B2 | 12/2014 | Meyers |
| 9,039,171 B2 | 5/2015 | Groisman |
| 9,063,352 B2 | 6/2015 | Ford et al. |
| 9,341,864 B2 * | 5/2016 | de Juan, Jr. ............ G02C 7/047 |
| 9,389,434 B2 | 7/2016 | Jubin et al. |
| 9,395,468 B2 | 7/2016 | Havenstrite |
| 9,442,307 B2 | 9/2016 | Meyers |
| 2006/0290882 A1 | 12/2006 | Meyers et al. |
| 2010/0001926 A1 | 1/2010 | Amirparviz |
| 2010/0118262 A1 | 5/2010 | Rosenthal |
| 2015/0234204 A1 | 8/2015 | Havenstrite |
| 2015/0312560 A1 | 10/2015 | Deering |
| 2016/0054589 A1 | 2/2016 | Otts |
| 2016/0216534 A1 * | 7/2016 | Legerton ................ G01B 21/08 |
| 2016/0266406 A1 * | 9/2016 | Meyers .................. B32B 27/40 |
| 2016/0379054 A1 | 12/2016 | Sicari et al. |
| 2017/0242269 A1 | 8/2017 | Havenstrite |
| 2017/0299892 A1 | 10/2017 | Pugh |
| 2017/0360994 A1 | 12/2017 | Havenstrite |

OTHER PUBLICATIONS

Holden, B.A. et al., "Critical Oxygen Levels to Avoid Corneal Edema for Daily and Extended Wear Contact Lenses," Investigative Ophthalmology & Visual Science, Oct. 1984, pp. 1161-1167, vol. 25, No. 10.
PCT International Search Report and Written Opinion, PCT Application No. PCT/US2018/016419, dated Apr. 4, 2018, 11 pages.

* cited by examiner

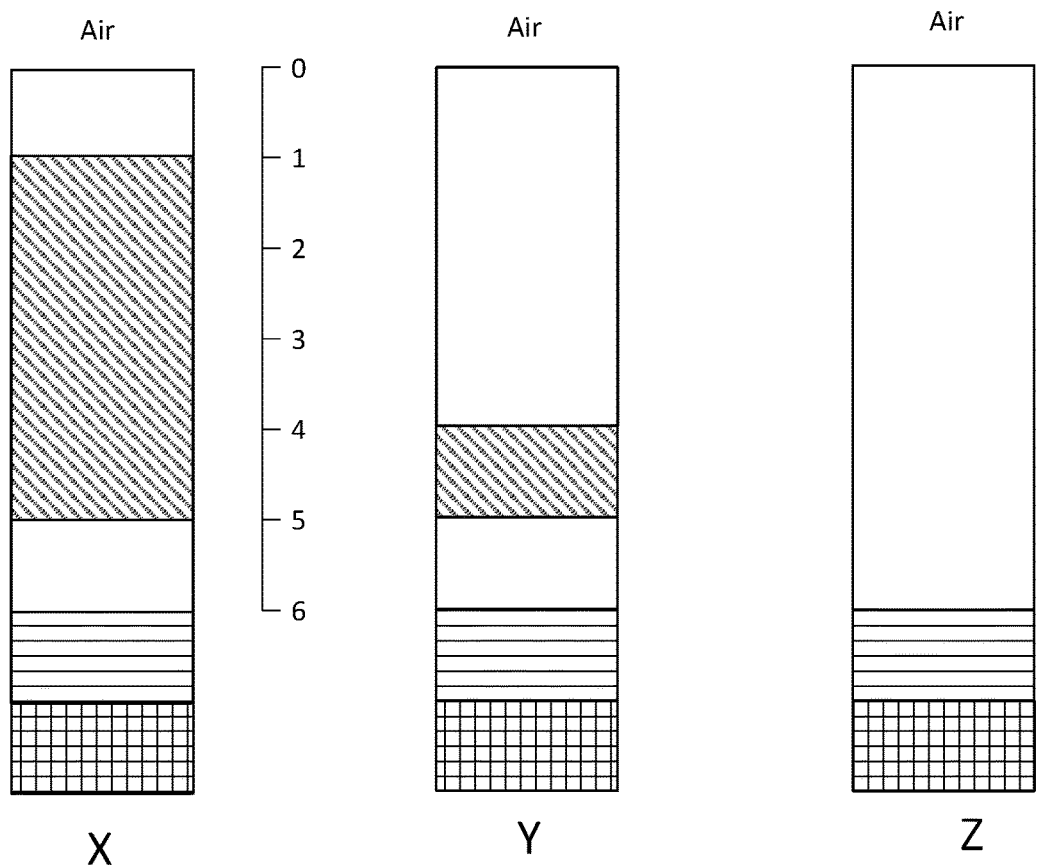
FIG. 7
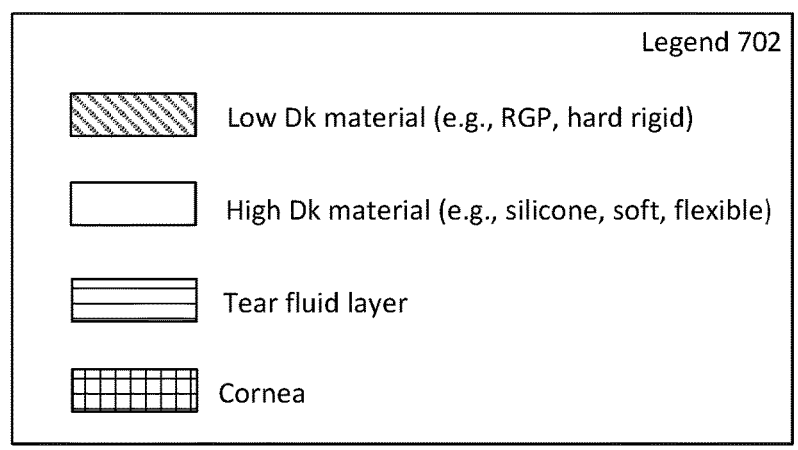

OXYGEN PERMEABLE CONTACT LENS STRUCTURES FOR THICK PAYLOADS

CROSS-REFERENCE TO RELATED APPLICATION(S)

This application claims priority under 35 U.S.C. § 119(e) to U.S. Provisional Patent Application Ser. No. 62/447,844, titled "Oxygen Permeable Contact Lens Structures for Thick Payloads," filed on Jan. 18, 2017, the subject matter of which is incorporated herein by reference in its entirety.

BACKGROUND

1. Technical Field

This invention generally relates to content lens structures, and in particular to oxygen permeable contact lens structures that can carry payloads.

2. Description of Related Art

Contact lenses that provide refractive vision correction are ubiquitous. In addition, therapeutic lenses may be used to treat eye diseases and injuries. For example, scleral contact lenses, which are supported at the periphery of the eye and form a tear-filled vault over the cornea, may be used to treat cornea disorders and severe dry eye syndrome, in addition to providing refractive vision correction.

Due to the lack of blood vessels within the human cornea, the tissue that makes up the cornea must receive oxygen through exposure to the air. As such, in order to maintain corneal health, any contact lens disposed over the cornea requires at least a threshold amount of oxygen permeability to allow for a sufficient amount of oxygen from the air to reach the cornea.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

FIG. 7 shows three different cross sections of a variable geometry contact lens structure carrying a payload, taken at different locations.

DETAILED DESCRIPTION OF THE PREFERRED EMBODIMENTS

Figure 1:
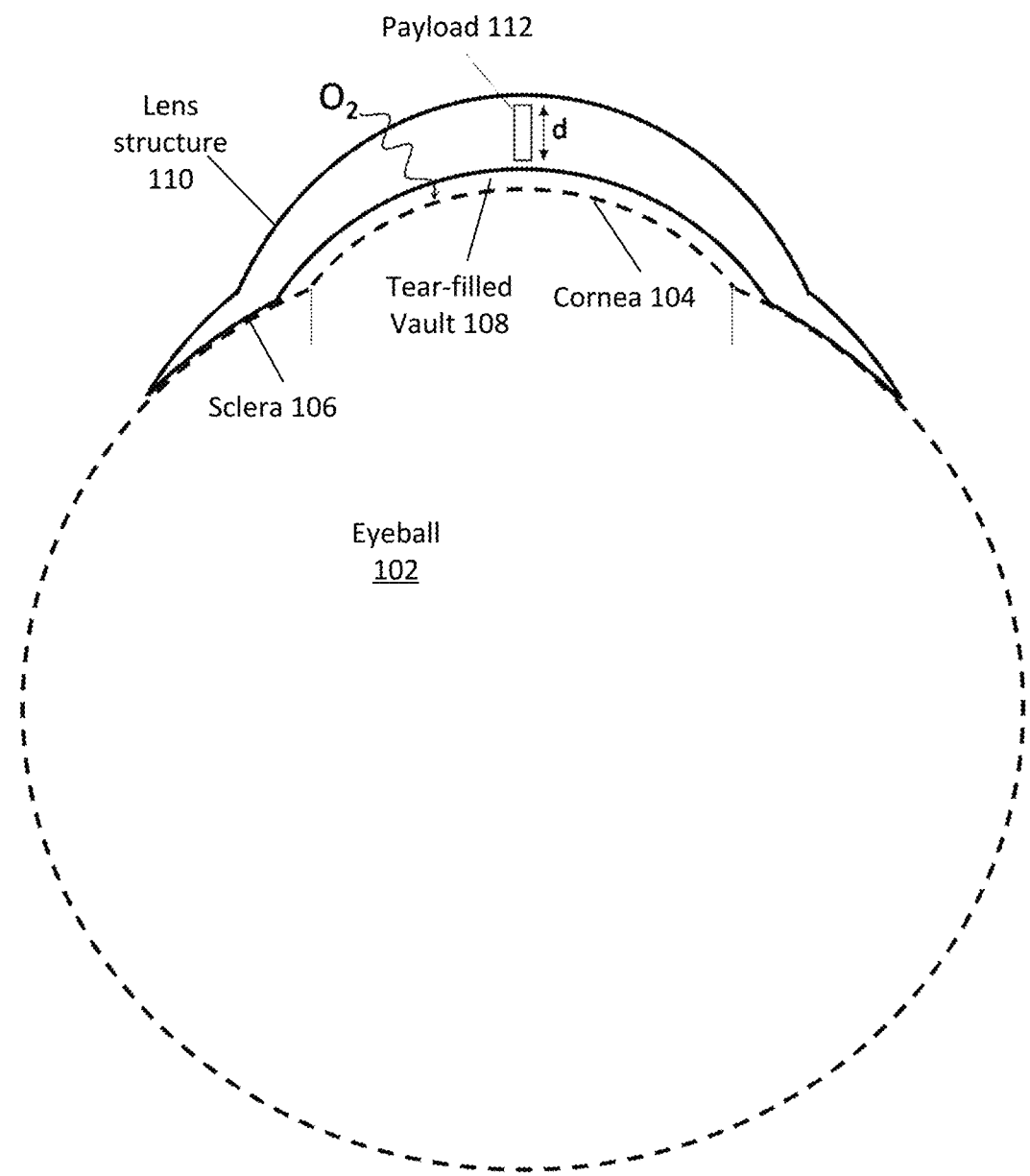
FIG. 1 shows a cross-sectional view of a scleral contact lens structure containing a payload.

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Various contact lens structures may be used to perform different functions. In some cases, the contact lens structure may contain active devices, which will be referred to as active payloads. For example, an active contact lens structure may contain a sensor device for monitoring glucose concentration in tear fluid, or for measuring intraocular pressure. As another example, a very small projector(s) and/or camera(s) may be contained in the contact lens structure, for example a "femtoprojector" as described by Deering in U.S. Pat. No. 8,786,675, "Systems using eye mounted displays", incorporated herein by reference. The projector may project images onto the wearer's retina, thus superimposing virtual objects onto the field of view of the wearer. Thus, when a person is wearing the contact lens display, he may see an augmented reality. Other active payloads may include other electronic, optical or microelectromechanical devices.

In order to embed a payload within a contact lens structure, the contact lens structure may be made thicker. However, increasing the thickness reduces the oxygen transmission to the cornea. In addition, relatively impermeable materials may be used to provide mechanical support for the payload, thus further reducing oxygen transmission to the cornea. Insufficient oxygen transmission to the cornea may quickly become intolerable for the wearer and may even lead to eye discomfort.

In one approach, a contact lens structure is constructed using layers of materials with high oxygen transmissibility and low oxygen transmissibility. The low transmissibility layer(s) have sufficient rigidity for providing mechanical support for the active payloads, and the high transmissibility layers provide adequate oxygen transmission. The ratio of the thicknesses of the two layers changes abruptly at the boundaries between the payload and non-payload regions of the structure. For convenience, these will be referred to as "variable geometry" contact lens structures.

In some designs, the low transmissibility material is the inner layer facing the eye. When rigid materials face the sclera, this can reduce potential slippage between the eye and the contact lens structure. Rigid gas permeable materials may offer good stiffness for mechanical support with some transmissibility. For example, a contact lens display with a femtoprojector may require some minimum stiffness in order to prevent the femtoprojector from shifting or moving relative to the wearer's eye, particularly if the femtoprojector is intended to always project images to the same part of the user's retina. However, rigid gas permeable materials thicker than a few hundred microns typically do not transmit enough oxygen to maintain corneal health. Examples of rigid gas permeable materials include HDS100 material, available from Paragon Vision Sciences, Inc., located in Mesa, Ariz., or fluorinated silicone materials. Conversely, the high transmissibility material may be an outer layer facing the external environment. Pure silicone (polysiloxanes) offers high oxygen transmissibility.

FIG. 1 shows a cross-sectional view of a scleral contact lens structure containing a payload. As illustrated in FIG. 1, the eye 102 includes a cornea 104 and a sclera 106. The scleral contact lens structure 110 is designed to contact the sclera 106 and to form a tear-filled vault 108 over the cornea 104. The contact lens structure 110 also includes a payload 112 of thickness d, which may be a femtoprojector. Oxygen permeates through the lens structure 110 to the cornea 104, based upon the oxygen transmissibility properties and thickness of the materials of the contact lens structure 110. In some embodiments, the contact lens structure may have a thickness of a few hundred microns above or below the payload in order to provide mechanical support for the payload 112.

In some embodiments, the contact lens structure 110 is constructed from a rigid gas permeable material having an oxygen transmissibility of approximately $$Dk \cong 100 \times 10^{-11} \left(\frac{cm^2}{sec}\right)\left(\frac{ml_{O_2}}{ml}\right)\left(\frac{1}{mmHg}\right),$$

commonly quoted as Dk="100", wherein D corresponds to a diffusion constant measured in $$\left(\frac{cm^2}{sec}\right),$$

and k corresponds to a concentration of $O_2$ per unit of $O_2$ partial pressure, and is measured in $$\left(\frac{ml_{O_2}}{ml}\right)\left(\frac{1}{mmHg}\right).$$

As such, a 200 micron thickness of this material has oxygen transmission $$Dk/t \cong 50 \times 10^{-9} \left(\frac{cm}{sec}\right)\left(\frac{ml_{O_2}}{ml}\right)\left(\frac{1}{mmHg}\right),$$

commonly quoted as Dk/t="50", wherein t corresponds to a thickness of the material.

For the purposes of corneal health and wearer comfort, a sufficient amount of oxygen is needed to reach the cornea of the wearer's eye (e.g., ~1 nL/sec). Dk/t functions as a metric indicating an amount of oxygen that is able to reach the cornea through a particular location on a contact lens structure, and may vary across the radius of the contact lens structure, based upon the thickness of materials that make up the contact lens structure. For example, the contact lens structure 110 illustrated in FIG. 1 may have a lower Dk/t near the center of the lens structure (due to greater material thickness) and a higher Dk/t in portions of the lens structure disposed over peripheral areas of the wearer's cornea (due to less material thickness). An aggregation of Dk/t across different areas of the contact lens structure may be used to determine an overall Dk/t of the contact lens structure, which is a simplified but convenient metric for oxygen flow. Analysis of oxygen flow that is more detailed than just calculating Dk/t typically will be performed to ensure adequate oxygenation of the cornea. Subject to this simplification, generally, an oxygen transmission corresponding to an overall Dk/t="24" is the minimum recommended for daily wear contact lenses, while an oxygen transmission of overall Dk/t="87" is the minimum recommended for extended wear lenses in contact with the cornea. See, e.g., Holden and Mertz, Investigative Ophthalmology and Visual Science 25:1161-1167, 1984. Dk can be measured in Barrers, where $$1 \text{ Barrer} = 10^{-10} \frac{cm^3_{STP} \cdot cm}{cm^2 \cdot sec \cdot cmHg} =$$

$$10^{-11} \frac{cm^3_{STP} \cdot cm}{cm^2 \cdot sec \cdot mmHg} = 10^{-11} \left(\frac{cm^3_{STP}}{cm^3}\right)\left(\frac{cm^2}{sec}\right)\left(\frac{1}{mmHg}\right),$$

and $cm_{STP}^3$ refers to a number of gas molecules that would occupy a space of 1 cubic centimeter (1 cc) at STP (standard temperature and pressure), as calculated using the ideal gas law.

In addition, because scleral lenses such as the contact lens structure 110 illustrated in FIG. 1 create a tear-filled vault (e.g., the tear-filled vault 108) between the lens structure 110 and the cornea 104, the oxygen transmission (Dk/t) of the tear-filled vault 108 must also be considered when determining an overall oxygen transmission of the contact lens structure. As such, a conventional rigid gas permeable scleral lens with a thickness greater than a few hundred microns typically will not satisfy oxygen transmission requirements. Due to these oxygen transmission requirements, conventional scleral contact lens structures typically cannot accommodate payloads of 500 to 1000 microns or more in thickness.

Figure 2:
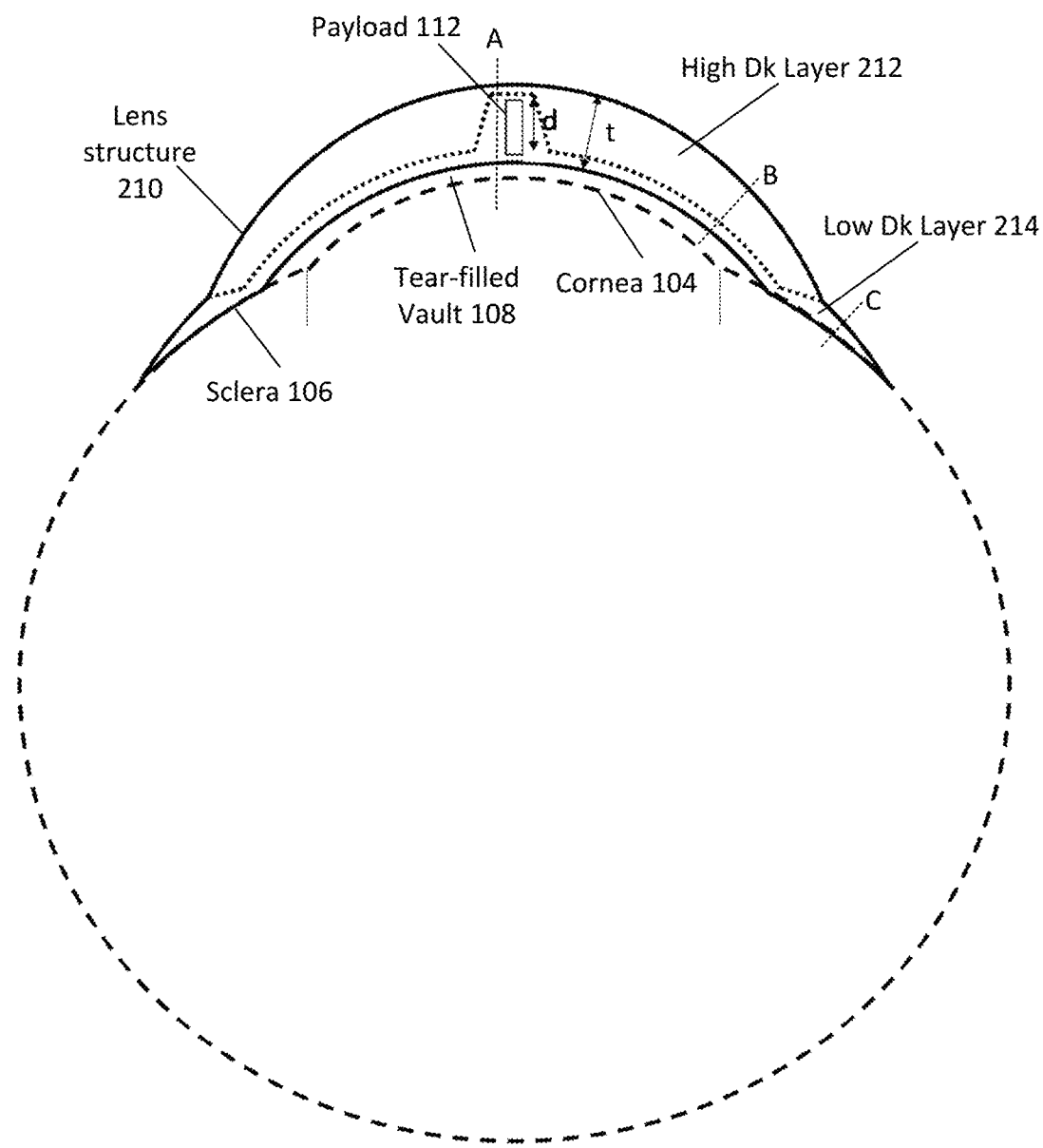
FIG. 2 shows a cross-sectional view of a variable geometry scleral contact lens structure containing a payload.

FIG. 2 shows a cross-sectional view of a variable geometry contact lens structure containing a payload. The lens structure 210 illustrated in FIG. 2 is a scleral contact lens. The contact lens structure 210 has a thickness t that is thick enough to accommodate the payload 112 having a thickness d. The contact lens structure 210 has a first layer 212 (also referred to as a "high Dk layer") and a second layer 214 (also referred to as a "low Dk layer"), made of a high transmissibility and a low transmissibility material, respectively.

The second layer 214 is constructed from a material having low oxygen transmissibility (Dk) and high stiffness, and is used to support the payload 112 and provide rigidity necessary to form the tear-filled vault 108 over the cornea 104. The first layer 212 fills in the rest of the lens structure 210, and is constructed using a material with high oxygen transmissibility (Dk) but usually low stiffness. For example, in the contact lens structure 210 of FIG. 2, the layer 212 of high Dk material forms the outer refractive surface of the contact lens.

The contact lens structure 210 of FIG. 2 has "variable geometry" in that the ratio of the thicknesses of the first and second layers 212 and 214 vary over different regions of the lens structure 210. For example, some areas of the contact lens structure 210, such as those near the payload 112 (e.g., point A), may contain a thin first layer 212 and a thick second layer 214, resulting in a low ratio of high Dk material to low Dk material, in order to provide sufficient low Dk material for supporting the payload 112 within the contact lens structure 210. Other areas of the contact lens structure 210 (e.g., point B) may contain a thick first layer 212 and a thin second layer 214, resulting in a high ratio of high Dk material to low Dk material.

If the payload 112 is a femtoprojector, in some embodiments, the layers of material of the contact lens structure 210 are configured such that a clear optical path, with no interfaces between different materials, is provided between the femtoprojector and the eye (e.g., only low Dk material between the femtoprojector and eye, as illustrated in FIG. 2). In some embodiments, the high and low Dk materials are selected to be index matched, in order to reduce refraction and reflection at the interfaces between the layers of high Dk material and low Dk material within the optical zone, since these may affect the wearer's view through the contact lens structure.

Because the rate of oxygen transmission at different locations of the lens structure 210 is based upon the oxygen transmissibility Dk and thickness t of the materials of the lens structure 210, the oxygen transmission at point B on the lens structure 210 is greater than that at point A, due to a larger ratio of the thickness of the lens being high Dk material instead of low Dk material. In some embodiments, the ratio of the relative thicknesses of the different layers within the lens structure 210 may differ by a factor of two or more. That is, if the high Dk material has thickness t1 and the low Dk material has thickness t2, then the ratio $R=t1/t2$ varies by more than 2:1 over the optical zone of the contact lens (i.e., the area through which light passes en route to the retina). In some embodiments, the ratio $R=t1/t2$ varies by more than 2:1 over the optical zone of the contact lens within a radial distance t corresponding to a maximum thickness of the lens structure. In some embodiments, some areas of the lens (e.g., point C) may have only low Dk material while others may have only high Dk material.

Figure 3:
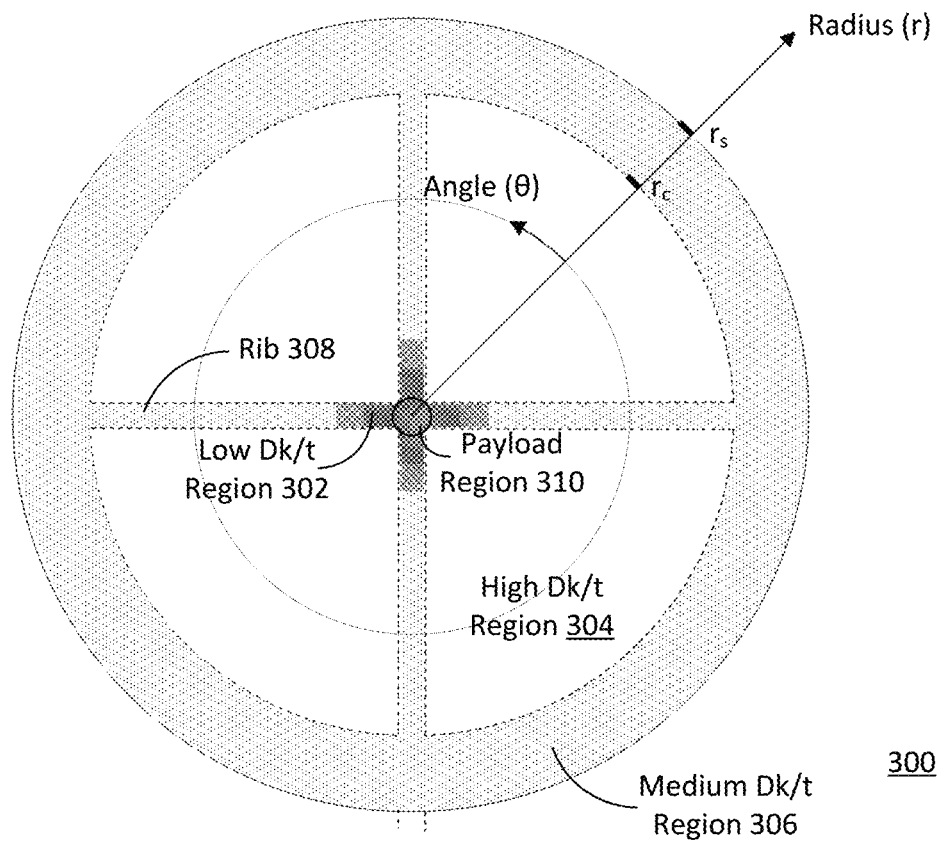
FIG. 3 shows a plan view of a variable geometry contact lens structure containing a payload.

FIG. 3 shows a plan view of a variable geometry contact lens structure containing a payload. For the sake of simplicity, FIG. 3 illustrates a top-down view of the contact lens structure 300, without consideration of the distortion inherent in a careful representation of the curved surface of a contact lens on a plane. This examples uses a polar coordinate system with radius, r, and angular coordinate, $\theta$. The contact lens structure 300 contains areas of high, medium and low Dk/t. Darker portions of the contact lens structure 300 illustrated in FIG. 3 (e.g., low Dk/t region 302) represent areas with overall lower Dk/t while lighter portions of the contact lens structure 300 (e.g., high Dk/t region 304) represent areas with overall higher Dk/t.

In FIG. 3, the area between radius rc and radius rs forms a ring-shaped medium Dk/t region 306. In some embodiments, the medium Dk/t region 306 comprises a medium Dk material such as a silicone hydrogel. Ribs or spokes 308 having medium Dk/t connect the ring-shaped medium Dk/t region 306 to the central low Dk/t region 302. While FIG. 3 illustrates four ribs 308, different designs may have fewer ribs, more ribs, and/or ribs of different shapes.

In some embodiments, the areas of high, medium and low Dk/t need not have radial or circumferential symmetry (N-fold symmetry) as illustrated in FIG. 3. In some embodiments, the radius rc may represent the maximum radius of a cornea while radius rs may represent a circle in the sclera of the wearer's eye.

The area at the center of the contact lens structure 300, inside the solid circle 310 may be referred to as the payload region, and corresponds to an area of the contact lens structure 300 designed to support one or more optical, electronic and/or micro-electromechanical devices (e.g., the payload 112) and any interconnections between devices. In some embodiments, the payload region 310 is located within the low Dk/t region 302, and, due to the presence of the payload 112, has an even lower Dk/t compared to the remainder of the low Dk/t region 302. Although FIG. 3 illustrates the low Dk/t region 302 and the payload region 310 as being located at the center of the contact lens structure 300 and at least partially surrounded by the high Dk/t region 304, in other embodiments, the payload region need not be in the center of a lens. There may also be multiple payloads, with a single large payload region or multiple disjoint payload regions.

The low Dk/t region 302 has a higher percentage of materials having an overall stiffness or rigidity sufficient to support the payload within the payload region 310. The medium Dk/t region 306 has materials having an overall stiffness or rigidity sufficient to support an edge of the contact lens structure 300 on the sclera of the wearer's eye and to support the ribs 308 to form a tear filled vault over the wearer's cornea. The high Dk/t region 304 has a higher percentage of materials having an overall Dk/t such that an aggregate Dk/t of the contact lens structure satisfies a minimum Dk/t threshold (e.g., a minimum Dk/t level for daily wear contact lens). The different regions of the contact lens structure 300 illustrated in FIG. 3 (e.g., low Dk/t region 302, high Dk/t region 304, and medium Dk/t region 306) are illustrated using a single level of shading in FIG. 3, but they may include different layers of materials having different levels of oxygen transmissibility. For example, the high Dk/t regions 304 may include a thick layer of high Dk material overlaid on a thin layer of low Dk material (e.g., similar to point B illustrated in FIG. 2), while the low Dk/t regions 302 may include a thick layer of low Dk material overlaid with a thin layer of high Dk material (e.g., similar to point A illustrated in FIG. 2).

Figure 4:
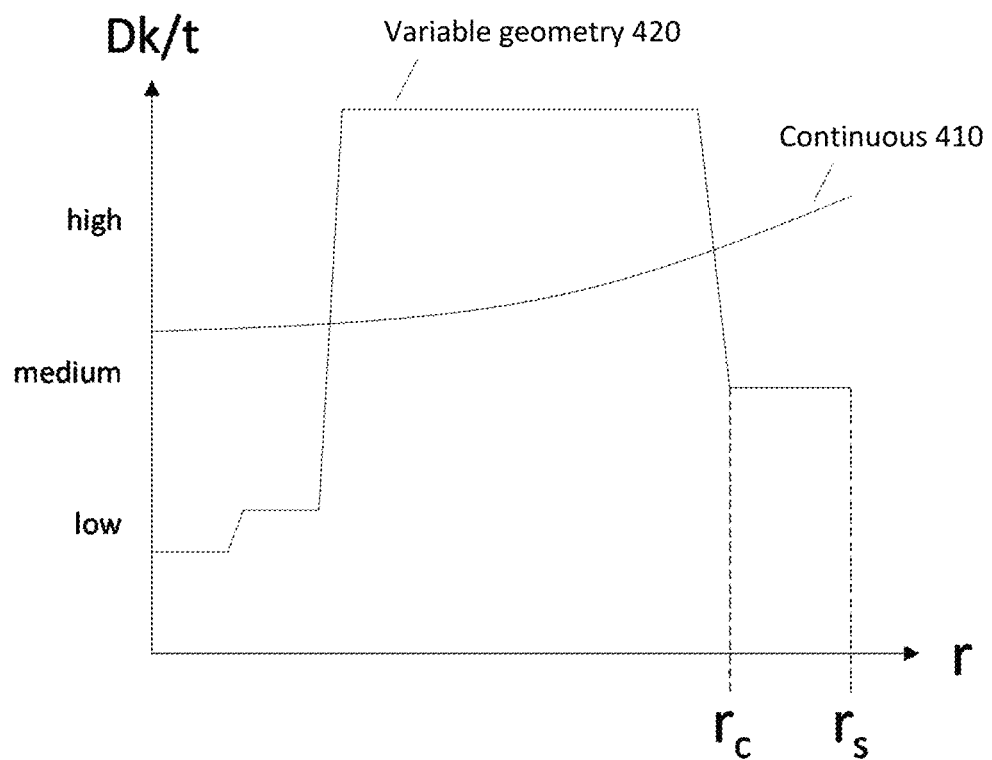
FIG. 4 is a graph of oxygen transmission as a function of radius, comparing two types of contact lenses.

FIG. 4 is a graph of oxygen transmission Dk/t as a function of radius r, comparing two types of contact lenses. The first curve 410 marked "continuous" shows Dk/t of a contact lens made from one or more layers of material but without variable geometry, such as the contact lens structure 110 shown in FIG. 1. The Dk/t of the "continuous" lens does not vary significantly over the radius of the lens. In contrast, the second curve 420 marked "variable geometry" illustrates Dk/t at different locations on a variable geometry lens, such as the contact lens structure 210 shown in FIG. 2 or the contact lens structure 300 shown in FIG. 3. The variable geometry curve 420 exhibits large and abrupt variations of Dk/t within the optical zone, due to large and abrupt variations of the ratio R between the high Dk and low Dk materials. In FIG. 4, the Dk/t and the thickness ratio R of the lens starts at an initial low value in the center of the lens ($r=0$) due to the payload. At the boundary of the payload region, the Dk/t and thickness ratio R increase abruptly. As one measure, the thickness ratio R of the thickness of the high Dk material to the thickness of the low Dk material increases by at least a factor of 2 over a lateral distance that is not more than the thickness t of the contact lens structure.

The transmission Dk/t drops again outside the corneal region (i.e., between radius rc and radius rs). The initial low Dk/t values near the center of the lens may correspond to the low Dk/t region 302 illustrated in FIG. 3, while the high values within the optical zone may correspond to the high Dk/t region 304, and the medium values outside the optical zones corresponding to the medium Dk/t region 306. In other embodiments, the lowest value of Dk/t may not occur in the center of the lens. For example, the supporting ring outside the optical zone may have a lower Dk/t than the center, allowing for a stiffer material to be used to provide support to the contact lens structure. Although FIG. 4 illustrates the Dk/t of the contact lens structure over the corneal region but outside the payload region as being substantially constant, the Dk/t of the contact lens structure may vary within the region. For example, as illustrated in FIG. 3, the thickness of high Dk layer 212 may be monotonically thinner as a function of radius r from the center of the contact lens structure outside the payload region, causing the Dk/t within the region to increase with increasing r within the corneal region. In other embodiments, the thickness of high Dk layer may be substantially constant outside the payload regions within the corneal region. In addition, the thickness of the low and/or medium Dk layers may also vary based on r (e.g., be monotonically thinner as a function of r in regions within the corneal region but outside the payload regions).

Figure 5:
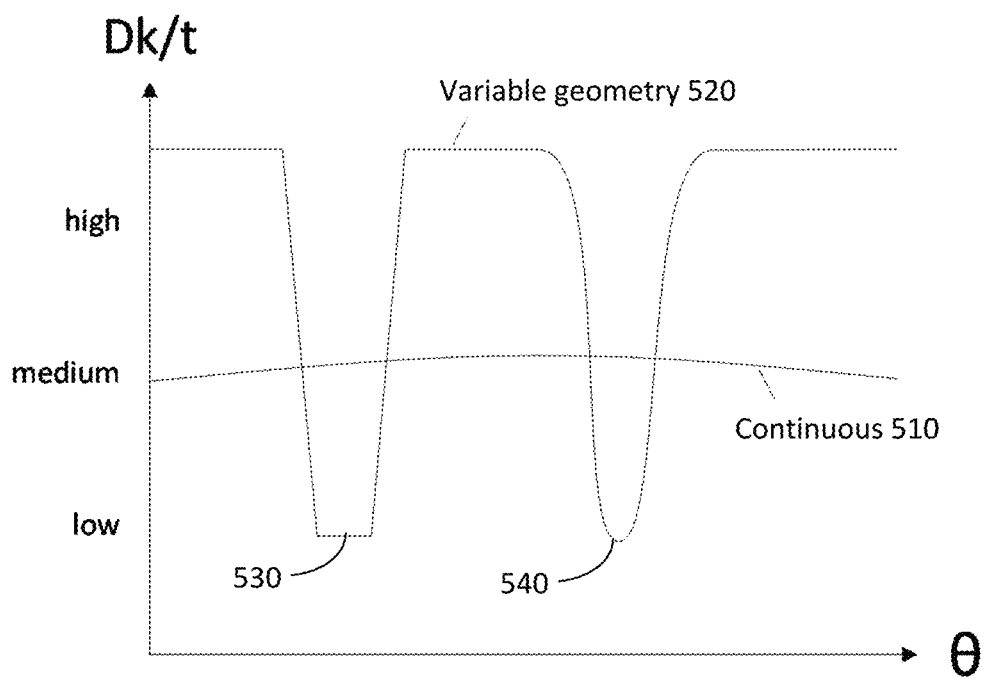
FIG. 5 is a graph of oxygen transmission as a function of angle, comparing two types of contact lenses.

FIG. 5 is a graph of oxygen transmission Dk/t as a function of angle θ, comparing two types of contact lenses. The particular radius value r corresponds to a radius within the optical zone of the contact lens structure but outside the payload region of the contact lens structure. Similar to FIG. 4, the first curve 510 marked "continuous" corresponds to a "continuous" contact lens that does not exhibit variable geometry along the θ coordinate. In contrast, the second curve 520 marked "variable geometry" plots Dk/t as a function of θ for a variable geometry lens such as the contact lens structure 300 illustrated in FIG. 3. This lens exhibits large and abrupt variations as a function of angle in the optical zone. For example, most of the optical zone falls within regions where Dk/t is high (e.g., high Dk/t region 304). However, Dk/t drops rapidly to a lower value in areas corresponding to ribs or spokes within the optical zone (e.g. ribs 308). Dk/t between the high Dk/t regions and the ribs may change sharply (e.g., at region 530 corresponding to a first rib) or smoothly (e.g., at region 540 corresponding to a second rib) as shown in the second curve 520.

Because variable geometry contact lens structures use different materials in layers of varying relative thicknesses, the Dk/t of the variable geometry lens within the high Dk/t region may be higher than the Dk/t of the continuous lens structure in the same region. As illustrated in FIGS. 4 and 5, the higher Dk/t of the variable geometry lens within the high Dk/t region may function to compensate for the lower Dk/t near the center of the lens structure needed to support the payload and/or at the periphery of the lens structure needed to support the edges of the lens on the sclera, such that the variable geometry lens as a whole allows for a sufficient amount of oxygen to reach the cornea of the wearer. In addition, because sufficient support for the contact lens structure may be provided by the low and medium Dk/t regions, the materials having higher Dk used in the high Dk/t regions may be less constrained by stiffness or rigidity requirements.

Figure 6:
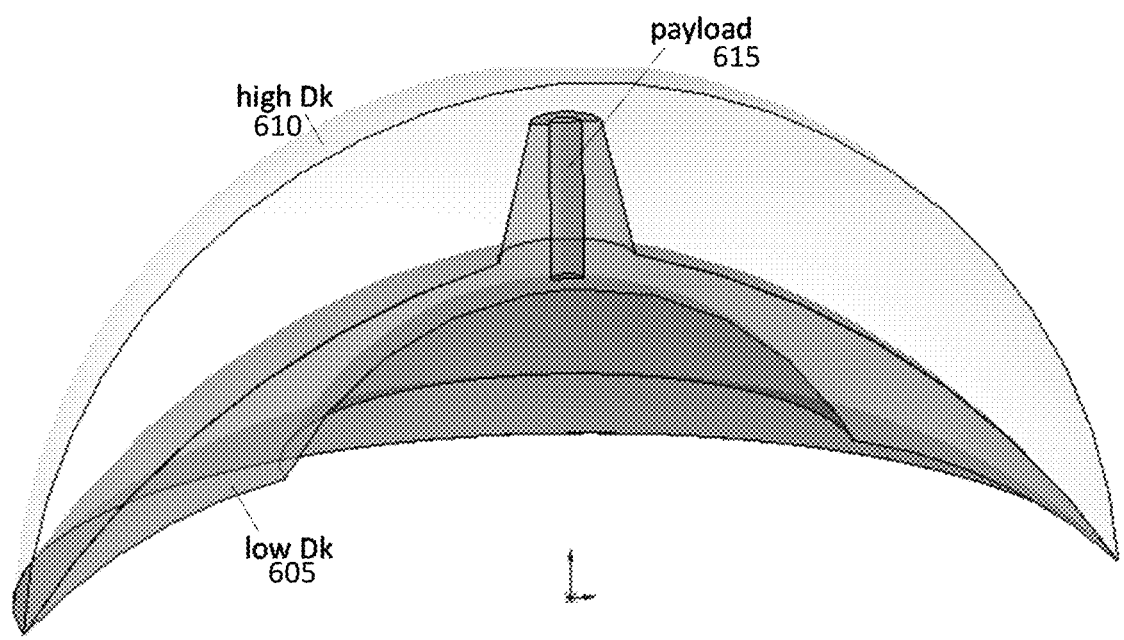
FIG. 6 is a three-dimensional, cut-away view of a variable geometry contact lens structure carrying a payload.

FIG. 6 is a three-dimensional, cut-away view of a variable geometry contact lens structure carrying a payload 615, in accordance with some embodiments. The lens contains both a low Dk, high stiffness layer 605 and a high Dk, low stiffness layer 610. In FIG. 6, the payload 615 is supported by a conical section of stiff low Dk material in the center of the lens extending as part of the low Dk layer 605. In other designs, the payload region containing the payload 615 need not be in the center of the lens and need not be conical, and there may be multiple payloads 615. In one approach, the payloads are treated as inserts to the contact lens structure. Without the payloads, the low Dk material would have a constant thickness across at least the optical zone (or slightly decreasing thickness toward the edge). The high Dk material would fill in the rest of the contact lens structure and therefore would have decreasing thickness toward the edge. The payloads are inserted into this base design.

FIG. 7 shows three different cross sections of a variable geometry contact lens structure, taken at different locations. The legend 702 identifies portions of the cross section corresponding to low Dk material, high Dk material, tear fluid, and cornea layers. Cross section X includes a thick, low Dk layer and thin high Dk layers. Cross section Y includes a thin low Dk layer and thick high-Dk layers. Cross section Z includes a thick high Dk layer and no low Dk layer.

Sections X, Y and Z may correspond to areas of low, medium and high Dk/t within a lens structure.

For purposes of illustration, the low Dk material in FIG. 7 is assumed to be a rigid gas permeable material with Dk=100, while the high Dk material may comprise silicone with Dk=500. The lenses of each of the cross sections X, Y and Z are illustrated as having a thickness of 6 arbitrary units. For example, cross section X has low Dk thickness of 4 units and high Dk thickness of 2 units, cross section Y has low Dk thickness of 1 unit and high Dk thickness of 5 units, and cross section Z has high Dk thickness of 6 units.

The composite Dk/t at each location can be computed based upon the Dk and thicknesses t of the materials at the location, in a manner similar to how electrical conductances are added in series. For example, the composite Dk/t for each of the illustrated cross sections may be expressed as:

$$\frac{1}{(Dk/t)_{Total}} = \frac{1}{(Dk/t)_1} + \frac{1}{(Dk/t)_2} + \ldots \quad (1)$$

In FIG. 7, therefore, the total "Dk/t" between the air and the tear layer above the cornea is, ignoring lateral diffusion, 23 for cross section X, 50 for cross section Y and 83 for cross section Z. In contrast, a location on a lens structure having a thickness of 6 units and comprising only the low Dk material would have a Dk/t of 17.

A variable geometry contact lens has different Dk/t values in different areas of the lens structure. For example, Dk/t and thickness ratio R may vary by a factor of two or greater within the optical zone (e.g., between the payload region and the high Dk/t regions outside the payload).

The tear fluid layer in FIG. 7 is shown as similar thickness to various layers of contact lens material. In some embodiments, the tear fluid layer between a scleral contact lens and a cornea may be as thick as 200-300 microns. However, different types of contact lenses may rest on a much thinner tear fluid layer. For example, a particular type of contact lens structure may have a shape that creates a thicker or thinner tear fluid layer above the cornea of the wearer.

Even though cross sections X, Y and Z in FIG. 7 have distinctly different values of Dk/t, if the three cross sections were adjacent to each other in a scleral contact lens and there was sufficient lateral flow, the flux of oxygen available to the cornea underlying the lens would be relatively uniform. The relative uniformity is obtained because oxygen is transported laterally in the contact lens (via diffusion) and in the tear fluid layer (via diffusion and convection) that exists under the scleral arch. In some embodiments, a contact lens structure may contain narrow regions having zero oxygen transmissibility. However, lateral oxygen transport from adjacent regions through high transmission layers or in the tear fluid layer may provide enough oxygen flux to the cornea, even in areas of the cornea under the regions of zero oxygen transmission. For example, some types of payloads that may be carried in a variable geometry contact lens structure are not oxygen permeable. However, corneal health may be maintained under such payloads if a tear fluid layer and/or an adjacent oxygen permeable layer provides lateral oxygen transport from high-Dk areas of the variable geometry lens structure to portions of the cornea under the payload area.

Figure 8:
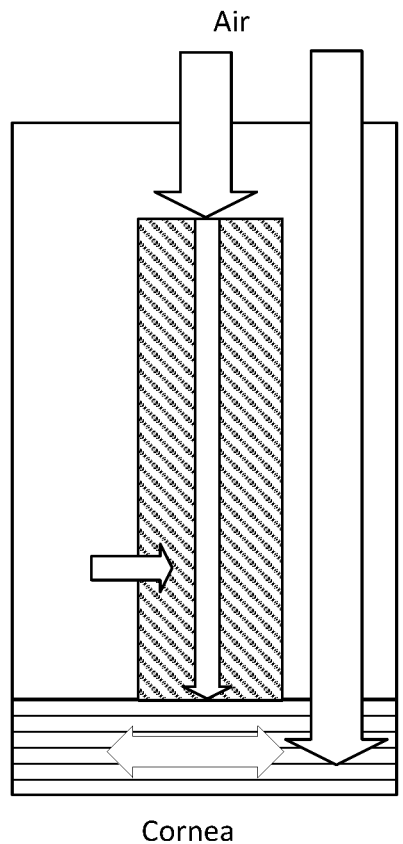
FIG. 8 illustrates lateral oxygen diffusion beneath a payload for a variable geometry contact lens containing a payload.

FIG. 8 illustrates lateral oxygen diffusion beneath a payload for a variable geometry contact lens containing a payload. Similar to FIG. 7, FIG. 8 includes a legend 802 identifying various materials in a cross section of a contact lens. The tear fluid layer is in contact with the cornea of the wearer (not shown in FIG. 8). The arrows in FIG. 8 illustrate oxygen flow, with the thickness of the arrow indicating a rate of the flow (i.e., thick arrows indicate high oxygen flow while thin arrows indicate low oxygen flow). As illustrated in FIG. 8, oxygen is transmitted more slowly through low Dk material compared to high Dk material. In addition, the tear fluid layer formed between the contact lens structure and the wearer's cornea is thick enough to provide a path for lateral oxygen transport (i.e. parallel to the surface of the cornea). Therefore oxygen may reach areas of the cornea that are underneath low Dk/t areas of the contact lens structure via lateral transport in the tear fluid layer.

Variable geometry contact lenses may be made with a combination of manufacturing techniques. High Dk materials such as rigid gas permeable plastic may be machined using precision lathe, milling, laser machining and/or polishing techniques. In some embodiments, radially asymmetric designs may be fabricated with multi-axis diamond turning machines. For example, a "fast tool servo" or fast c-axis on a diamond turning machine may be used to fabricate the abrupt transitions between different areas of the contact lens structure. Low Dk materials such as pure silicones may be cast or molded to form other parts of a lens structure. Such materials may be over-cast onto rigid structures, or molded in a mold and cured, and later transferred and bonded to the rigid material. Plasma treatments may be used to promote adhesion between different materials such as plastics, polymers, and silicones as needed. In some embodiments, high Dk and low Dk materials may be index matched to reduce or eliminate reflections and refraction at high Dk-low Dk interfaces.

Variable geometry allows thick payloads to be carried in a contact lens without sacrificing cornea health due to oxygen starvation. Structural rigidity is provided by low-oxygen-transmissibility materials that are confined to payload regions and support ribs or other support structures. High oxygen transmission is provided by high-oxygen-transmissibility materials that make up much of the area of the lens. Oxygen flow is provided to areas of the cornea that lie underneath payload regions and support ribs by lateral diffusion of oxygen in high-oxygen-transmissibility layers of the lens and/or tear fluid layers separating the lens from the cornea. Oxygen transmission of variable geometry lenses may vary by more than a factor of two between different areas in the optical zone (e.g., between the high Dk/t regions and the low Dk/t regions).

The foregoing description of the embodiments of the invention has been presented for the purpose of illustration; it is not intended to be exhaustive or to limit the invention to the precise forms disclosed, but merely illustrates different examples. It should be appreciated that the scope of the disclosure includes other embodiments not discussed in detail above. Persons skilled in the relevant art can appreciate that many modifications and variations are possible in light of the above disclosure, without departing from the spirit and scope as defined in the appended claims. Therefore, the scope of the invention should be determined by the appended claims and their legal equivalents.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A contact lens structure having a maximum thickness t, comprising:
    in an optical zone of the contact lens:
        a first layer characterized by an oxygen transmissibility $Dk1$ that would be high enough to provide sufficient oxygen to the cornea if the first layer had a thickness $t1=t$;
        a second layer that provides mechanical support for a payload, the second layer characterized by an oxygen transmissibility $Dk2$ that would not be high enough to provide sufficient oxygen to the cornea if the second layer had a thickness $t2=t$;
        a payload region disposed between the first and second layers, the payload region configured to contain the payload; and
        where, at a boundary of the payload region, a ratio of thicknesses of the first layer to the second layer, $R=t1/t2$, changes by at least 2:1 over a lateral distance of not more than t.

2. The contact lens structure of claim 1, where the payload includes active electronics.

3. The contact lens structure of claim 1, where the payload includes a femtoprojector.

4. The contact lens structure of claim 1 where, in the optical zone, the contact lens structure comprises a plurality of payload regions each configured to contain a payload.

5. The contact lens structure of claim 4, where the payload regions are disjoint and regions between payload regions have ratios R of thicknesses of the first layer to the second layer that are at least 2× greater than the ratios R within the payload regions.

6. The contact lens structure of claim 1, where the oxygen transmissibility $Dk1$ of the first layer is at least 100.

7. The contact lens structure of claim 1, where the first layer is a silicone layer.

8. The contact lens structure of claim 1, where the oxygen transmissibility $Dk2$ of the second layer is not more than 100.

9. The contact lens structure of claim 1, where the second layer is a rigid gas permeable layer.

10. The contact lens structure of claim 1, where the second layer is a fluorinated silicone layer.

11. The contact lens structure of claim 1, where the first layer is an outer layer of the contact lens structure.

12. The contact lens structure of claim 1, where the second layer is an inner layer of the contact lens structure.

13. The contact lens structure of claim 1, where the contact lens structure is a scleral contact lens structure.

14. The contact lens structure of claim 1 where:
    in the optical zone, the contact lens structure comprises one or more payload regions; and
    outside the payload region(s), the thickness t1 of the first layer is monotonically thinner as a function of radius r from a center of the contact lens structure.

15. The contact lens structure of claim 1 where:
    in the optical zone, the contact lens structure comprises one or more payload regions; and outside the payload region(s), the thickness t2 of the second layer is constant.

16. The contact lens structure of claim 1 where:
in the optical zone, the contact lens structure comprises one or more payload regions; and
outside the payload region(s), the thickness t2 of the second layer is monotonically thinner as a function of radius r from a center of the contact lens structure.

17. The contact lens structure of claim 1 where:
in the optical zone, the contact lens structure comprises one or more payload regions; and
outside the payload region(s), the second layer has a spoke structure to provide mechanical support for the payload region(s).

18. The contact lens structure of claim 1 where, in the optical zone, the ratio R varies as a function of an angle $\theta$ measured from a center of the contact lens structure.

19. The contact lens structure of claim 1 where, in the optical zone, the ratio R has N-fold symmetry with respect to an angle $\theta$ measured from a center of the contact lens structure.

20. The contact lens structure of claim 1 wherein the first and second layers comprise solid materials.

* * * * *